United States Patent [19]

Sarpotdar et al.

[11] Patent Number: 4,942,158

[45] Date of Patent: Jul. 17, 1990

[54] TRANSDERMAL STEROID PENETRANT COMPOSITIONS AND METHODS UTILIZING ISOPROPANOL AND ISOBUTANOL

[75] Inventors: Pramod P. Sarpotdar, Malvern, Pa.; Tammy B. Strassburg, Rochester, N.Y.

[73] Assignee: Eastman Kodak, Rochester, N.Y.

[21] Appl. No.: 257,374

[22] Filed: Oct. 13, 1988

[51] Int. Cl.$^5$ ............................................. A61K 31/56
[52] U.S. Cl. .................................... 514/170; 514/169; 514/177; 514/182; 514/947
[58] Field of Search ............... 514/169, 182, 177, 170, 514/947

[56] References Cited

U.S. PATENT DOCUMENTS

| | | | |
|---|---|---|---|
| 3,787,571 | 1/1974 | Higuchi | 514/170 |
| 4,460,372 | 7/1984 | Campbell et al. | 604/897 |
| 4,593,048 | 6/1986 | Sato et al. | 514/778 |
| 4,710,497 | 12/1987 | Heller et al. | 514/221 |
| 4,775,529 | 10/1958 | Sequeira et al. | 514/170 |

FOREIGN PATENT DOCUMENTS 2158355 5/1985 United Kingdom .

Primary Examiner—Joseph A. Lipovsky
Attorney, Agent, or Firm—Irving Newman

[57] ABSTRACT

A unique combination of isopropyl and isobutyl alcohols synergistically increases the permeability of the skin to steroid drugs.

20 Claims, No Drawings

TRANSDERMAL STEROID PENETRANT COMPOSITIONS AND METHODS UTILIZING ISOPROPANOL AND ISOBUTANOL

FIELD OF THE INVENTION

This invention relates to the field of transdermal administration of drugs. More particularly, it relates to the enhancement of transdermal delivery of steroid drugs.

DESCRIPTION RELATIVE TO THE PRIOR ART

Transdermal administration of drugs offers several therapeutic and compliance advantages over the more traditional routes of administration. A major drawback of this therapy, however, is the limitation on the amount of drug that can be transported across the skin. This limitation is due to several factors. Since the skin is a protective barrier by nature, the rates of transport of most compounds through the skin are quite slow. Also, even though the skin is the largest single organ, there aren't many areas on the body where its surface is flat. Therefore, as a practical matter, transdermal drug delivery patches must have a relatively small surface area. It is generally accepted that a surface area of the patch beyond 30 to 50 cm$^2$ would result in difficulty of application due to the contours of the skin. Moreover, drug permeability varies greatly between skins of different individuals.

It is thus important to increase the rates of penetration of drugs across the skin so that a wider variety of drugs can be administered by transdermal therapy. While steroids are relatively poorly permeable to skin, it has become desirable to administer this class of drugs transdermally, and transdermal patches for delivery of steroids have become available.

Increasing the permeability of the skin to steroids would allow an increased degree of control in the system for drugs with moderate permeabilities.

Aliphatic alcohols are commonly used in topical/transdermal formulations as cosolvents. U.S. Pat. No. 4,460,372 makes use of ethanol as a permeation enhancer. UK Patent Application GB 2,158,355A discloses the use of a combination of propylene glycol and glycerine to enhance the transdermal penetration of therapeutic agents. U.S. Pat. No. 4,593,048 describes the use of a combination of a monohydric lower alcohol having 1 to 4 carbon atoms with at least one of (a) a saturated aliphatic hydrocarbon, (b) a carboxylic acid alcohol ester, and (c) an ether to improve skin permeation and percutaneous absorption of drugs.

SUMMARY OF THE INVENTION

The present invention makes use of a particular combination of isopropyl alcohol (IPA) and isobutyl alcohol (IBA) to enhance the transdermal penetration of steroids. More particularly, it has been found that, while use of either of these solvents alone does not enhance the penetration of estradiol through cadaver skin in vitro, when these solvents are used in combination in approximately equal amounts (w/w), the rate of penetration of estradiol is increased at least two-fold.

Thus, in one aspect, the present invention provides a topical composition for the transdermal delivery of a steroid drug which comprises a therapeutically effective amount of a steroid drug in a vehicle comprising a mixture of isopropyl alcohol and isobutyl alcohol, each of these alcohols being present in an amount of from about 45% to about 55% by weight based on the weight of said mixture.

In another embodiment, the invention provides a method for enhancing the rate of transdermal delivery of a steroid drug, this method comprising contacting the skin with a composition comprising said steroid and a vehicle which comprises a mixture of isopropyl alcohol and isobutyl alcohol, each of these alcohols being present in an amount of from about 45% to about 55% by weight based on the weight of said mixture.

In yet another embodiment, the invention comprises a device for transdermal delivery of a steroid drug, in which device the vehicle for the steroid drugs comprises a mixture of IPA and IBA, each of these alcohols being present in an amount of from about 45% to about 55% by weight, based on the weight of said mixture.

DETAILED DESCRIPTION OF THE INVENTION

A preferred steroid for use in the compositions and methods of the present invention is estradiol. For certain applications, it is desirable to use a combination of estradiol and a progestogen; such as progesterone or medroxy progesterone.

The compositions of the present invention may also include, in the vehicle, in addition to the mixture of substantially equal amounts of IPA and IBA, other pharmaceutically acceptable carrier liquids compatible therewith and with the steroid or steroids employed. A particularly preferred additional carrier liquid is water, which is preferably present in an amount of up to 50% by weight, based on the total weight of the vehicle.

While the IPA and IBA may each be present in the mixture in an amount of from about 45% to about 55% by weight, based on the total weight of the mixture, it is preferred that the range be from about 47% to about 53%. More preferably, the range is from about 49% to about 51%.

It has been found that, when water is included in the vehicle, a gelling agent such as methocel (methyl cellulose) or PVP (polyvinylpyrrolidine) may also be included. Other commonly used adjuvants, such as antioxidants, surfactants and the like may also be incorporated in the vehicle.

Transdermal drug delivery devices in accordance with the present invention may comprise any conventional transdermal patch construction employing pharmaceutically acceptable materials that are compatible with the steroid drug and with the drug delivery vehicle comprising the IBA/IPA mixture of the present invention (as described above). Typically, the device, or transdermal patch, will comprise an impervious backing layer, a drug containing layer comprising the steroid drug in admixture with a vehicle of the present invention, a spreading layer, an adhesive layer and a release lining. Selection of particular patch designs as well as of particular materials of construction will be routine matters to those skilled in the art.

The following examples are presented to illustrate the practice of the present invention.

EXAMPLE 1

Table I shows the compositions of 5 test formulations. Each formulation contains a sufficient amount of estradiol to make a saturated solution of estradiol. Thus, the rates of penetration of estradiol through cadaver skin would be similar if the diffusivity of estradiol through the cadaver skin is the only controlling factor. However, Table II clearly shows that the rate of penetration of estradiol at least doubles when the solvent composition comprises a 50:50 w/w mixture of IPA/IBA. The data shown in Table II were obtained by testing the formulations of Table I in accordance with the following procedure.

A piece of human cadaver skin was placed over the opening of a Franz extraction cell filled with saline solution, with the stratum corneum facing the donor compartment and the dermal side facing the receptor, and was set in place and stretched taut by inserting the glass ring (a glass cover with the center open to add sample) and clamping to hold in position. The skin was equilibrated to physiological saline overnight at 37° C.

Samples of drug and skin penetration-enhancing agents having the compositions shown in Table I were prepared, and each formulation was tested by placing a 0.5 mL sample onto the skin through the opening in the ring that forms the top of the cell (after equilibration) sealing the cell with a screw cap, and allowing the extraction to continue for 7 days.

Periodically, the receiver solution in the cell was removed and replaced with fresh saline. A typical sampling schedule is after 0, 48, 72, 96, 120, 144, and 168 hours. The concentration of drug in the removed saline solution was determined by liquid scintillation counting or high performance liquid chromatography (HPLC) techniques after each sampling. The flux for each composition was calculated from the terminal linear portions of the curve, plotting cumulative amount penetrated vs time, and is reported in Table II for each formulation as the average from 4 runs.

Table II also reports the time lag ($t_L$) before reaching steady state delivery of drug to the saline, and the calculated area of skin, i.e., the size that a transdermal drug delivery patch would have to be in order to deliver 50 μg of estradiol per day.

TABLE I

| Ingredient* | Test Formulations Concentration (% w/w) | | | | |
|---|---|---|---|---|---|
| Formulation: | I | II | III | IV | V |
| Estradiol | 10.5 | 5.5 | 7.0 | 10.5 | 5.5 |
| IPA | 89.5 | 23.6 | 46.5 | 67.1 | — |
| IBA | — | 70.9 | 46.5 | 22.4 | 94.5 |

*IPA = Isopropyl alcohol;
IBA = Isobutyl alcohol.

TABLE II

| | Summary of the Results | | |
|---|---|---|---|
| Formulation | Flux mcg/cm$^2$/hr | $t_L$ hrs | Avg. Patch size (cm$^2$) |
| IPA (I) | 0.74 | 46.8 | 2.8 |
| 75/25 IPA/IBA (IV) | 0.82 | 36.8 | 2.8 |
| 50/50 IPA/IBA (III) | 1.42 | 36.1 | 1.5 |
| 25/75 IPA/IBA (II) | 0.46 | 39.0 | 4.5 |
| IBA (V) | 0.54 | 40.2 | 3.9 |

The invention has been described in detail with particular reference to preferred embodiments thereof, but it will be understood that variations and modifications can be effected within the spirit and scope of the invention.

We claim:

1. A topical composition for the transdermal delivery of a steroid drug which comprises a therapeutically effective amount of a steroid drug in a vehicle comprising a mixture of isopropyl alcohol and isobutyl alcohol, each of these alcohols being present in an amount of from about 45% to about 55% by weight based on the weight of said mixture.

2. The composition of claim 1 wherein said range is from about 47% to about 53% by weight.

3. The composition of claim 1 wherein said range is from about 49% to about 51% by weight.

4. The composition of claim 1 wherein said steroid drug comprises estradiol.

5. The composition of claim 4 wherein said steroid drug further comprises progesterone or medroxy progesterone.

6. The composition of claim 4 wherein said vehicle further comprises water.

7. The composition of claim 6 wherein said vehicle comprises methyl cellulose.

8. The composition of claim 1 wherein said steroid drug comprises a progestogen.

9. The composition of claim 1 wherein said vehicle further comprises water.

10. The composition of claim 9 wherein said vehicle further comprises methyl cellulose.

11. A topical composition for the transdermal delivery of a steroid drug which comprises a therapeutically effective amount of a steroid drug in a vehicle comprising substantially equal concentrations, by weight, of isopropyl alcohol and isobutyl alcohol.

12. The composition of claim 11 wherein said vehicle further comprises water.

13. A method for enhancing the rate of transdermal delivery of a steroid drug, this method comprising contacting the skin with a composition comprising said steroid and a vehicle which comprises substantially equal concentrations, by weight, of isopropyl alcohol and isobutyl alcohol.

14. The method of claim 13 wherein said steroid drug comprises estradiol.

15. The method of claim 14 wherein said steroid drug further comprises a progestogen.

16. The method of claim 13 wherein said vehicle further comprises water.

17. The method of claim 16 wherein said vehicle further comprises methyl cellulose.

18. In a transdermal patch for delivering a steroid drug to a patient, the improvement wherein the vehicle for said steroid drug comprises a mixture of isopropyl alcohol and isobutyl alcohol, each of these alcohols being present in an amount of from about 45% to about 55% by weight based on the weight of said mixture.

19. The transdermal patch of claim 18 wherein said vehicle further comprises water.

20. The transdermal patch of claim 19 wherein said vehicle further comprises methyl cellulose.

* * * * *